(12) United States Patent
Franciskovich et al.

(10) Patent No.: US 10,183,087 B2
(45) Date of Patent: Jan. 22, 2019

(54) CLEANING AND DISINFECTING COMPOSITION

(71) Applicant: American Sterilizer Company, Mentor, OH (US)

(72) Inventors: Phillip P. Franciskovich, Concord, OH (US); Donald G. Rosenhamer, Medina, OH (US); Kathleen A. Fix, Willoughby, OH (US)

(73) Assignee: American Sterilizer Company, Mentor, OH (US)

( * ) Notice: Subject to any disclaimer, the term of this patent is extended or adjusted under 35 U.S.C. 154(b) by 65 days.

(21) Appl. No.: 14/936,775

(22) Filed: Nov. 10, 2015

(65) Prior Publication Data

US 2017/0128605 A1    May 11, 2017

(51) Int. Cl.
*C11D 3/02* (2006.01)
*C11D 1/75* (2006.01)
(Continued)

(52) U.S. Cl.
CPC .............. *A61L 2/18* (2013.01); *A01N 37/02* (2013.01); *A01N 37/16* (2013.01); *A01N 59/00* (2013.01);
(Continued)

(58) Field of Classification Search
CPC .. C11D 1/72; C11D 1/722; C11D 1/75; C11D 3/0073; C11D 3/33; C11D 1/662; C11D 3/2041; C11D 3/2044; C11D 3/38636; C11D 3/22; C11D 3/222; C11D 3/3902; C11D 3/3942; C11D 3/3945; C11D 3/30; B08B 3/04

USPC ....... 510/303, 336, 337, 356, 372, 402, 421, 510/434, 477, 488, 499, 505, 506, 470, 510/161, 238, 245, 254, 255, 258, 264; 134/42

See application file for complete search history.

(56) References Cited

U.S. PATENT DOCUMENTS 5,037,623 A    8/1991    Schneider et al.
5,077,008 A    12/1991    Kralovic et al.
(Continued)

FOREIGN PATENT DOCUMENTS

EP    2436265    4/2012
WO    2004020562    3/2004
WO    2012028196    3/2012

OTHER PUBLICATIONS

Andreev et al.; "Volatile Corrosion Inhibitors Based on Ethanolamines"; Protection of Metals; vol. 33, No. 5, Sep. 1, 1997.
(Continued)

*Primary Examiner* — Gregory R Delcotto
(74) *Attorney, Agent, or Firm* — Renner, Otto, Boisselle & Sklar, LLP

(57) ABSTRACT

The disclosed invention relates to a two-part liquid composition for cleaning and disinfecting a substrate, comprising: (A) a disinfectant medium comprising peracetic acid; and (B) a supplemental medium comprising a non-enzymatic cleaner, a corrosion inhibitor, and a chelator. The supplemental medium (B) may further comprise an enzymatic cleaner, a surfactant, a buffer, a pH modifier, or a mixture of two or more thereof. The substrate may be a medical device, for example, an endoscope.

39 Claims, 8 Drawing Sheets

(51) Int. Cl.

| | | |
|---|---|---|
| C11D 3/395 | (2006.01) | |
| C11D 3/39 | (2006.01) | |
| A61L 2/18 | (2006.01) | |
| C11D 1/722 | (2006.01) | |
| A01N 37/02 | (2006.01) | |
| A01N 37/16 | (2006.01) | |
| A01N 59/00 | (2006.01) | |
| A01N 59/02 | (2006.01) | |
| C11D 1/66 | (2006.01) | |
| C11D 1/72 | (2006.01) | |
| C11D 3/00 | (2006.01) | |
| C11D 3/386 | (2006.01) | |
| C11D 3/48 | (2006.01) | |
| C11D 1/88 | (2006.01) | |
| C11D 1/90 | (2006.01) | |
| C11D 3/04 | (2006.01) | |
| C11D 3/20 | (2006.01) | |
| C11D 3/22 | (2006.01) | |
| C11D 3/28 | (2006.01) | |
| C11D 3/30 | (2006.01) | |
| C11D 3/33 | (2006.01) | |
| C11D 3/36 | (2006.01) | |
| C11D 3/37 | (2006.01) | |
| C11D 7/10 | (2006.01) | |
| C11D 7/26 | (2006.01) | |
| C11D 7/32 | (2006.01) | |
| C11D 7/36 | (2006.01) | |
| C11D 11/00 | (2006.01) | |
| A61B 1/005 | (2006.01) | |
| A61B 1/12 | (2006.01) | |
| B08B 3/08 | (2006.01) | |

(52) U.S. Cl.
CPC .............. *A01N 59/02* (2013.01); *A61B 1/005* (2013.01); *A61B 1/125* (2013.01); *A61L 2/186* (2013.01); *B08B 3/08* (2013.01); *C11D 1/66* (2013.01); *C11D 1/662* (2013.01); *C11D 1/72* (2013.01); *C11D 1/722* (2013.01); *C11D 1/75* (2013.01); *C11D 1/88* (2013.01); *C11D 1/90* (2013.01); *C11D 3/0073* (2013.01); *C11D 3/046* (2013.01); *C11D 3/2068* (2013.01); *C11D 3/2075* (2013.01); *C11D 3/2082* (2013.01); *C11D 3/2086* (2013.01); *C11D 3/225* (2013.01); *C11D 3/28* (2013.01); *C11D 3/30* (2013.01); *C11D 3/33* (2013.01); *C11D 3/361* (2013.01); *C11D 3/364* (2013.01); *C11D 3/365* (2013.01); *C11D 3/3707* (2013.01); *C11D 3/38618* (2013.01); *C11D 3/38627* (2013.01); *C11D 3/38636* (2013.01); *C11D 3/3947* (2013.01); *C11D 3/48* (2013.01); *C11D 7/10* (2013.01); *C11D 7/263* (2013.01); *C11D 7/265* (2013.01); *C11D 7/3218* (2013.01); *C11D 7/3245* (2013.01); *C11D 7/3281* (2013.01); *C11D 7/36* (2013.01); *C11D 11/0041* (2013.01); *A61L 2202/17* (2013.01); *A61L 2202/24* (2013.01)

(56) References Cited

U.S. PATENT DOCUMENTS

| | | | | |
|---|---|---|---|---|
| 5,998,342 | A | * | 12/1999 | Scoville, Jr. .............. C11D 1/94 134/42 |
| 6,017,871 | A | * | 1/2000 | Baeck ....................... A61K 8/22 510/125 |
| 6,057,277 | A | * | 5/2000 | Crudden .................. C11D 1/10 510/392 |
| 6,235,692 | B1 | * | 5/2001 | Scoville ................... C11D 1/94 134/40 |
| 6,369,011 | B1 | * | 4/2002 | Rai .......................... C11D 3/386 51/221 |
| 6,448,062 | B1 | | 9/2002 | Huth et al. |
| 7,569,532 | B2 | * | 8/2009 | Man ........................ C11D 3/046 510/337 |
| 7,597,766 | B2 | | 10/2009 | McRae et al. |
| 7,642,224 | B2 | | 1/2010 | McRae et al. |
| 7,648,583 | B2 | | 1/2010 | McRae et al. |
| 7,754,671 | B2 | * | 7/2010 | Lin .......................... C11D 3/373 510/276 |
| 8,293,174 | B2 | | 10/2012 | Kaiser et al. |
| 8,329,632 | B2 | | 12/2012 | Mikkelsen et al. |
| 8,530,184 | B2 | | 9/2013 | Franciskovich et al. |
| 8,691,562 | B2 | | 4/2014 | Franciskovich et al. |
| 2005/0020466 | A1 | * | 1/2005 | Man ........................ C11D 3/046 510/392 |
| 2005/0245418 | A1 | * | 11/2005 | Fregonese .......... C11D 3/38672 510/392 |
| 2006/0205626 | A1 | * | 9/2006 | Gant ........................ A01N 59/04 510/367 |
| 2010/0009884 | A1 | * | 1/2010 | Kritzler ................ C11D 3/0026 510/161 |
| 2011/0201536 | A1 | * | 8/2011 | O'Connell ........... C11D 3/2041 510/321 |
| 2011/0207649 | A1 | * | 8/2011 | Molinaro ............... C11D 3/046 510/382 |
| 2012/0021489 | A1 | * | 1/2012 | Chaudhuri ............. C11D 3/386 435/202 |
| 2012/0230870 | A1 | | 9/2012 | Franciskovich et al. |
| 2013/0260438 | A1 | * | 10/2013 | Alekseyev ............. C11D 3/386 435/221 |
| 2014/0311529 | A1 | * | 10/2014 | Nishio ..................... C11D 1/83 134/22.14 |
| 2015/0305342 | A1 | | 10/2015 | Burke et al. |

OTHER PUBLICATIONS

Muralidharan et al.; "Ethanolamines as Corrosion Inhibitors for Pure Nickel in Sulphuric Acid Solutions"; Bulletin of Electrochemistry, vol. 1, No. 4, Jul. 1, 1985.

International Search Report and Written Opinion for corresponding PCT International Application No. PCT/US2016/033395, dated Aug. 8, 2016.

\* cited by examiner

CLEANING AND DISINFECTING COMPOSITION

TECHNICAL FIELD

This invention relates to compositions that are useful for cleaning and disinfecting substrates and, more particularly, to two-part liquid compositions for cleaning and disinfecting substrates such as medical devices (e.g., endoscopes), and the like.

BACKGROUND

Medical devices such as endoscopes and the like, which are exposed to blood and other body fluids, require cleaning and disinfecting between each use. A problem in the art relates to the need for a cleaning and disinfecting system that can be used to clean and disinfect devices, such as endoscopes, that cannot withstand the high temperatures of steam sterilization. This invention provides a solution to this problem.

SUMMARY

This invention relates to a two-part liquid composition for cleaning and disinfecting a substrate, comprising: (A) a disinfectant medium comprising peracetic acid; and (B) a supplemental medium comprising a non-enzymatic cleaner, a corrosion inhibitor and a chelator; wherein the non-enzymatic cleaner comprises an alkanol amine, an alcohol ethoxylate, an alkyl glucoside, an alkylene glycol, an alkyl diproprionate, an alkyl dialkylamine oxide, or a mixture of two or more thereof. The disinfectant medium (A) may be referred to as part (A), and the supplemental medium (B) may be referred to as part (B). The supplemental medium (B) may be used as a cleaner and a builders medium and therefore may be referred to as a cleaners/builders medium. The supplemental medium may further comprise an enzymatic cleaner. The supplemental medium (B) may further comprise a surfactant, a buffer, a pH modifier, or a mixture of two or more thereof. The disinfectant medium (A) and the supplemental medium (B) may be diluted with water.

This invention relates to a process for cleaning and disinfecting a substrate using the above-indicated two-part liquid composition. This process is advantageous in that it is suitable for cleaning and disinfecting substrates, such as medical devices and the like, including endoscopes, that cannot withstand the high temperatures of steam sterilization.

In an embodiment, this invention relates to a one-step process for cleaning and disinfecting a substrate using the two-part liquid composition referred to above, the process comprising: contacting the substrate with the supplemental medium (B) and the disinfectant medium (A) to clean and disinfect the substrate. This process can be conducted at a temperature in the range from about 15° C. to about 60° C., or from about 18° C. to about 60° C., or from about 18° C. to about 56° C., or from about 18° C. to about 50° C., or from about 18° C. to about 40° C., or from about 18° C. to about 30° C., or from about 18° C. to about 24° C. The contacting time may be in the range from about 0.5 to about 240 minutes, or from about 2 to about 60 minutes.

In an embodiment, this invention relates to a two-step process for cleaning and disinfecting a substrate using the above-indicated two-part liquid composition, the process comprising the steps of (1) contacting the substrate with the supplemental medium (B) to clean the substrate; and (2) contacting the substrate with the disinfectant medium (A) to disinfect the substrate. In an embodiment, the two-step process comprises the steps of (1) contacting the substrate with the supplemental medium (B) and the disinfectant medium (A) to clean the substrate, and (2) contacting the substrate with the disinfectant medium (A) to disinfect the substrate. In an embodiment, the two-step process comprises the steps of (1) contacting the substrate with the supplemental medium (B) to clean the substrate, and (2) contacting the substrate with the disinfectant medium (A) and the supplemental medium (B) to disinfect the substrate. In an embodiment, the two-step process comprises the steps of (1) contacting the substrate with the supplemental medium (B) and the disinfectant (A) to clean the substrate, and (2) contacting the substrate with the disinfectant medium (A) and the supplemental medium (B) to disinfect the substrate. This process may optionally include rinsing the substrate subsequent to step (1) but prior to step (2). Each of steps (1) and (2) may be conducted at a temperature in the range from about 15° C. to about 60° C., or from about 18° C. to about 60° C., or from about 18° C. to about 56° C., or from about 18° C. to about 50° C., or from about 18° C. to about 40° C., or from about 18° C. to about 30° C., or from about 18° C. to about 24° C. The contacting time for each of steps (1) and (2) may be in the range from about 0.5 to about 240 minutes, or from about 2 to about 60 minutes.

In an embodiment, the above-indicated process may be used to provide a 4 or a 5 log reduction (for high level disinfectant (HLD) purposes), or a 6 log reduction (for sterilization purposes) of viable microorganisms, including spores, clinically significant bacteria, pathogenic viruses, and the like. In an embodiment, the process may be used to clean and disinfect a substrate. In an embodiment, the process may be used to clean and sterilize a substrate.

In an embodiment, the above-indicated process may be used to reduce the bio-load of patient soil (and or simulative soils commonly accepted by the FDA as representing worse case bio-load) to a level less than about 6 micrograms per square centimeter.

In an embodiment, the above-indicated process may be used to provide separate cleaning and disinfection steps while simultaneously minimizing the deleterious effects to the materials of construction of the substrates (e.g., endoscopes) being treated.

In an embodiment, the above-indicated process may be conducted at ambient conditions (about 18-24° C.), thus enabling use in reprocessors with or without temperature controls.

In an embodiment, the above-indicated process may be used at temperatures from ambient to about 60° C., thus enabling use in reprocessors with ranges of temperature controls from ambient up to about 60° C.

In an embodiment, the above-indicated process may be used in a wide variety of existing "open" automated endoscope reprocessing machines with minimum adaptations of the endoscope reprocessors.

In an embodiment, the above-indicated process may allow for the disinfectant medium (A) to remain stable with respect to concentration over the exposure phase of the reprocessing cycle when used at room temperatures (about 18-24° C.).

In an embodiment, the above-indicated process may allow for the disinfectant medium (A) to remain stable with respect to concentration over a period of time that spans multiple reprocessing cycles when used at room temperatures (about 18-24° C.).

In an embodiment, the supplemental medium (B) may employ a rinsing aid component to facilitate rinsing of the substrate (e.g., endoscope) being treated. In an embodiment, the supplemental medium (B) may employ an anti-foam component to reduce foaming.

The above-indicated two-part liquid composition may be used in a wide range of existing automated endoscope reprocessors (AERs). These may include AERs made by many manufacturers of "open" systems, as well as dedicated "closed" systems that have their own dedicated chemistries.

The above-indicated process may be used in static soak applications (no machine).

BRIEF DESCRIPTION OF THE DRAWINGS

In the annexed drawings, like references indicate like parts and features.

DETAILED DESCRIPTION

Figure 1:
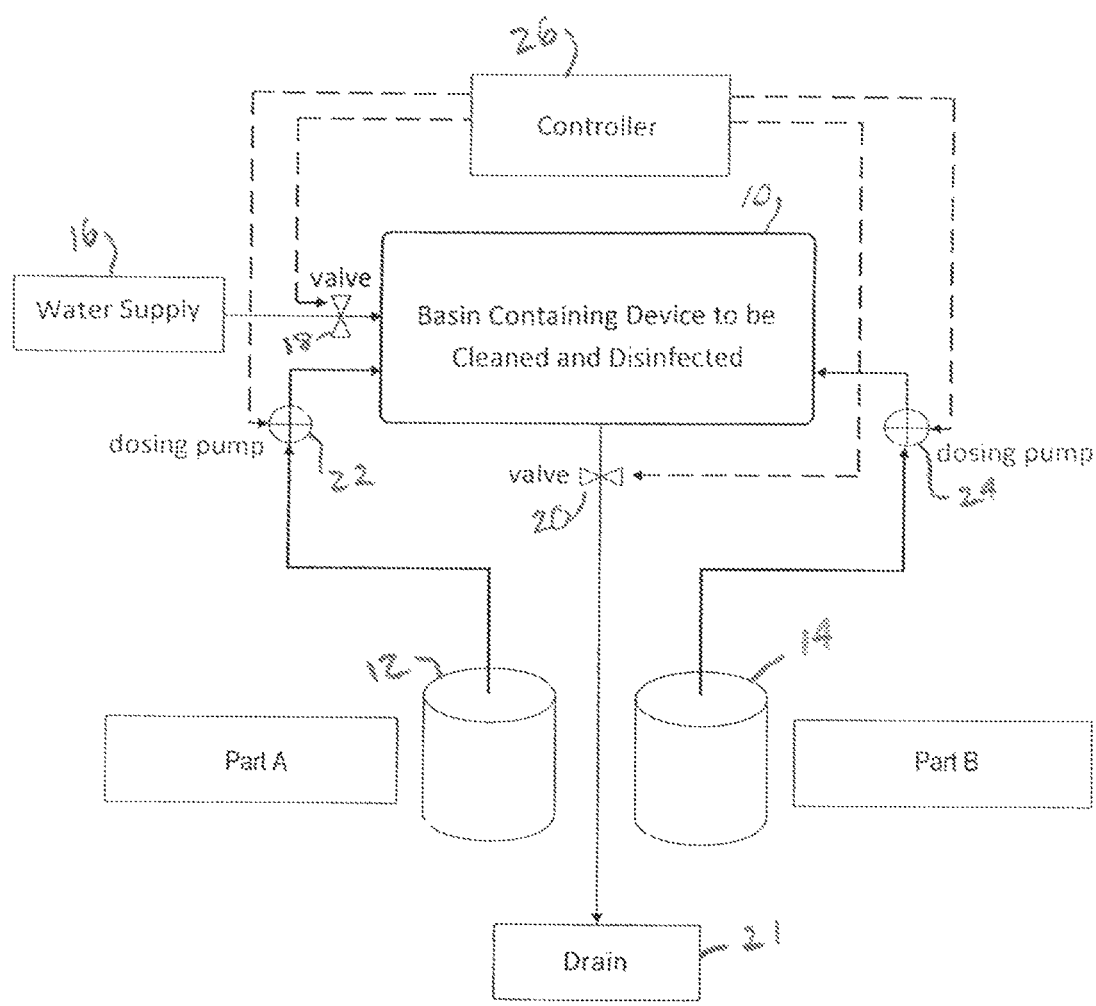
FIG. 1 is a schematic illustration of an apparatus used for a cleaning and disinfecting process in accordance with the invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "X and/or Y," when used in conjunction with open-ended language such as "comprising" can refer, in one embodiment, to X without Y (optionally including elements other than Y); in another embodiment, to Y without X (optionally including elements other than X); in yet another embodiment, to both X and Y (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of X and Y" (or, equivalently, "at least one of X or Y," or, equivalently "at least one of X and/or Y") can refer, in one embodiment, to at least one, optionally including more than one, X, with no Y present (and optionally including elements other than Y); in another embodiment, to at least one, optionally including more than one, Y, with no X present (and optionally including elements other than X); in yet another embodiment, to at least one, optionally including more than one, X, and at least one, optionally including more than one, Y (and optionally including other elements); etc.

The transitional words or phrases, such as "comprising," "including," "carrying," "having," "containing," "involving," "holding," and the like, are to be understood to be open-ended, i.e., to mean including but not limited to.

The term "killing" (or "kill") of a microorganism refers to rendering the microorganism incapable of returning to vegetative growth. In an embodiment, the term killing of a microorganism refers to rendering the microorganism incapable of reproduction, metabolism and/or growth.

The term "log reduction" is a mathematical term to show the number of live microorganisms killed by contacting the microorganisms with the inventive composition. A "4 log reduction" means that the number of live microorganisms is 10,000 times smaller. A "5 log reduction" means that the number of live microorganisms is 100,000 times smaller. A "6 log reduction" means that the number of live microorganisms is 1,000,000 times smaller.

The term "enzymatic cleaner" refers to a cleaning agent that is produced by a living organism. The enzymatic cleaner may be a lipase, amylase, carbohydrase or protease enzymatic cleaner.

The term "non-enzymatic cleaner" refers to a cleaning agent that is not an enzymatic cleaner.

The two-part liquid composition provided for herein may be used to clean a substrate and achieve at least a 4 log reduction, or at least a 5 log reduction, or at least a 6 log reduction in the number of undesirable microorganisms on the substrate capable of returning to or resuming vegetative growth or infection, or in an embodiment, capable of reproduction, metabolism and/or growth. These microorganisms may include spores, clinically significant bacteria, pathogenic viruses, mixtures of two or more thereof, and the like. When a 6 log reduction is achieved, the process may be referred to as a sterilization process. A 6 log reduction may be referred to as a 6 log kill. When a 4 log reduction or a 5 log reduction is achieved, the process may be considered to be less rigorous than a sterilization process, but nevertheless useful for various disinfecting applications. The term "disinfectant" (and "disinfecting") may be used herein to refer to disinfections, for example, high-level disinfections (HLD), as well as sterilizations. These may include log reductions in the number of undesirable living microorganisms of at least about 4, or at least about 5, or at least about 6.

The disinfectant medium (A) and the supplemental medium (B) may be sold and, optionally, used in concentrate form. The concentrates may be diluted with water prior to or during use. The water may be taken from any source. The water may comprise deionized water, tap water, processed tap water, mixtures thereof, and the like. The water may comprise soft water. The term "soft water" is used herein to refer to water with a hardness level in the range from 0 to about 60 milligrams per liter (mg/L as calcium carbonate).

The disinfectant medium (A) may be used to provide a disinfection or sterilization of the substrate being cleaned and disinfected. The disinfectant medium (A) may comprise water and peracetic acid. The concentration of peracetic acid in the disinfectant medium (A) may be in the range from about 5% to about 60% by weight, or from about 15% to about 45% by weight, or from about 30% to about 40% by weight, or about 35.5% by weight. The disinfectant medium (A) may optionally further comprise one or more additional ingredients, including acetic acid, hydrogen peroxide, sulfuric acid, or a mixture of two or more thereof. The concentration of acetic acid in the disinfectant medium (A) may be in the range up to about 62% by weight, or from about 34% to about 62% by weight, or from about 40% to about 55% by weight. The concentration of hydrogen peroxide in the disinfectant medium (A) may be in the range up to about 60% by weight, or from about 5% to about 60% by weight, or from about 6.5% to about 32% by weight. The concentration of sulfuric acid in the disinfectant medium (A) may be in the range up to about 2% by weight, or from about 0.5% by weight to about 2% by weight, or from about 0.75% to about 1.5% by weight. The concentration of water in the disinfectant medium (A) may be in the range up to about 60% by weight, or from about 5% to about 60% by weight, or from about 10% to about 50% by weight. A commercially available peracetic acid solution which may be used as the disinfectant medium (A) is available from FMC Corporation under the trade designation Peracetic Acid 35%. This solution contains about 35.5% by weight peracetic acid, about 40% by weight acetic acid, about 6.5% by weight hydrogen peroxide, about 1% by weight sulfuric acid, and about 17% by weight water. These compositions with the indicated concentrations may be useful for sale as concentrates, and optionally, for use in the inventive cleaning and disinfecting process. The concentrations may be diluted with water prior to or during use.

The supplemental medium (B) may be used to clean the substrate. In the case of a medical device, such as an endoscope, this may involve removal of residual foreign material or soil such as blood, feces, respiratory secretions, and the like. The supplemental medium (B) may comprise water, a non-enzymatic cleaner, a corrosion inhibiting agent and a chelator. The supplemental medium (B) may further comprise an enzymatic cleaner. The supplemental agent (B) may further comprise a buffer, a surfactant, a pH modifier, or a mixture of two or more thereof. Other additive ingredients may also be included in the supplemental medium (B). The supplemental medium (B) may be referred to as a cleaning/builders formulation. The term "builders" is used herein to refer to a combination of non-active ingredients that may be included in a cleaning or disinfecting composition. The non-active ingredients may be referred to as being non-active because they do not directly result in a cleaning or disinfection, but they are used for other purposes. These other purposes may include pH control, water softening (chelation), corrosion inhibition, and the like.

The non-enzymatic cleaner may comprise a surfactant with detergent or other cleaning properties. The non-enzymatic cleaner may be referred to as a surfactant cleaner. The non-enzymatic cleaner may be used to remove soil (e.g., blood, body fluids, and the like) from the substrate being cleaned. The non-enzymatic cleaner may comprise an alkanol amine, an alcohol ethoxylate, an alkyl glucoside, an alkylene glycol, an alkyl diproprionate, an alkyl dialkylamine oxide, or a mixture of two or more thereof. The alkanol amine may comprise monoethanol amine, diethanol amine, triethanolamine, or a mixture of two or more thereof. A commercially available alcohol ethoxylate that may be used is Berol 508 (an alcohol ethoxylate available from Akzo Nobel). The alkyl glucoside may comprise any glycoside that is derived from glucose. The alkyl glucoside may comprise decyl glucoside. The alkyl glucoside may comprise an alkyl polyglucoside. The alkyl polyglucoside may be derived from one or more sugars and one or more fatty alcohols. A commercially available alkyl glucoside that may be used is available from Alzo Nobel under the tradename AG 6206. The alkylene glycol may comprise a polyalkylene glycol with a molecular weight in the range from about 100 to about 5000, or from about 100 to about 1500. The polyalkylene glycol may comprise polyethylene glycol, polyproylene glycol, or a mixture thereof. The alkyl diproprionate may comprise octyl diproprionate. A commercially available octyl diproprionate that may be used is available from Solvay-Rhodia under the tradename Mackam ODP 45M. The alkyl dialkyamine oxide may comprise octyl dimethylamine oxide. The concentration of the non-enzymatic cleaner in the supplemental medium (B) may be in the range from about 0.1 to about 25% by weight, or from about 1 to about 25% by weight, or from about 5 to about 15% by weight. These concentrations may be suitable for sale as concentrates, and optionally for use in the inventive cleaning and disinfecting process. The concentrates may be diluted with water prior to or during use.

The corrosion inhibitor may comprise benzotriazole, a sodium salt of benzotriazole, tolyltriazole, a sodium salt of tolyltriazole, aminotrimethylene phosphonic acid, octyl betaine, a carboxylic acid such as Irgacro L-190 (an organic carboxylic acid available from BASF), ethanolamine, phosphonobutane tricarboxylic acid, or a mixture of two or more thereof. A commercially available sodium benzotriazole that may be used is available under the trade designation Cobratec 40S which is 40% by weight aqueous solution of sodium benzotriazole. The concentration of the corrosion inhibitor in the supplemental medium (B) may be in the range from about 1% by weight to about 10% by weight, or from about 1% by weight to about 5% by weight. These concentrations may be suitable for sale as concentrates and, optionally, for use in the inventive cleaning and disinfecting process. The concentrations may be diluted with water prior to or during use.

The chelator may comprise ethylenediaminetetraacetic acid, hydroxyethylidenediphosphonic acid, a sodium salt of either of these acids, aminotrimethylene phosphonic acid, phosphonobutane tricarboxylic acid, sodium hexametaphosphate, trisodium nitrilotriacetate monohydrate, sodium salt of polyacrylic acid, tetrasodium salt of glutamic acid diacetic acid, a polycarboxylic acid, tetrasodium iminodisuccinate, carboxymethyl inulin, sodium borate, methylglycine diacetic acid, or a mixture of two or more thereof. A useful sodium salt of ethylenediaminetetraacetic acid may be ethylenediaminetetraacetic acid, tetrasodium salt, tetrahydrate. A commercially available ethylenediaminetetraacetic acid, tetrasodium salt, tetrahydrate that may be used is available from Akzo Nobel under the trade designation Dissolvine 220-S. Dissolvine 220-S is identified by Akzo Nobel as being a chelating agent containing 83-85% by weight ethylenediaminetetraacetic acid, tetrasodium salt, tetrahydrate. The chelator may comprise a dicarboxylic acid and/or a tricarboxylic acid. The chelator may comprise citric acid. The concentration of the chelator in the supplemental medium (B) may be in the range from about 0.1% by weight to about 70% by weight, or from about 0.3% by weight to about 60% by weight, or from about 0.5% by weight to about 55% by weight. These concentrations may be suitable for sale as concentrates and, optionally, for use in the inventive cleaning and disinfecting process. The concentrations may be diluted with water prior to or during use.

The enzymatic cleaner may comprise a lipase, an amylase, a carbohydrase, a protease, or a mixture of two or more thereof. The enzymatic cleaner may comprise a protein hydrolyzing enzyme, a protein digesting enzyme, or a mixture thereof. The enzymatic cleaner may comprise a proteolytic enzyme. The enzymatic cleaner may comprise a subtilisin. Examples of commercially available enzymes that may be used include Alcalase Ultra 2.5L and Savinase 16L, Type EX (both of which are subtilisins available from Novozymes). The enzyme may be used in combination with the other ingredients of the supplemental medium (B) to break down the soil being treated (e.g., blood, body fluids, waste, etc.) to facilitate removal of the soil from the substrate. The concentration of the enzymatic cleaner in the supplemental medium (B) may be in the range up to about 25% by weight, or from about 0.2 to about 25% by weight, or from about 0.5 to about 10% by weight. These concentrations may be suitable for sale as concentrates and, optionally, for use in the inventive cleaning and disinfecting process. These concentrations may be diluted with water prior to or during use.

The buffer may comprise an alkali metal phosphate, an alkali metal carbonate, or a mixture thereof. The alkali metal may comprise sodium or potassium. The buffer may comprise one or more of monosodium phosphate, disodium phosphate, trisodium phosphate, monopotassium phosphate, dipotassium phosphate, tripotassium phosphate, sodium carbonate, sodium bicarbonate, or a mixture of two or more thereof. Disodium phosphate may be used. The concentration of the buffer in the supplemental medium (B) may be in the range up to about 15% by weight, or from about 1% by weight to about 15% by weight, or from about 4% by weight to about 10% by weight. These concentrations may be suitable for sale as concentrates and, optionally, for use in the inventive cleaning and disinfecting process. These concentrations may be diluted with water prior to or during use.

The surfactant may comprise a compound that lowers the surface tension (or interfacial tension) between the ingredients in the composition, or between the composition and the substrate being treated by the composition. The surfactant may comprise a wetting agent, emulsifier, foaming agent and/or dispersant. The surfactant may comprise a compound that contains at least one hydrophobic group and at least one hydrophilic group. The surfactant may comprise both a water insoluble (or oil soluble) component and a water soluble component. The surfactant may comprise one or more ionic (e.g., anionic, cationic and/or zwitterionic) and/or nonionic compounds. The surfactant may comprise one or more polyethylene glycol ethers, alkylarylsulfonates, amine oxides, poly(oxyalkylene) compounds, block copolymers comprising alkylene oxide repeat units, carboxylated alcohol ethoxylates, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan esters, imidazoline and/or derivatives thereof, lecithin and/or derivatives thereof, lignin and/or derivatives thereof, glycerides and/or derivatives thereof, olefin sulfonates, phosphate esters and/or derivatives thereof, propoxylated and/or ethoxylated fatty acids and/or alcohols, alkyl phenols, sorbitan and/or derivatives thereof, sucrose esters and/or derivatives thereof, sulfates and/or alcohols and/or ethoxylated alcohols of fatty esters, sulfonates of dodecyl and/or tridecyl benzenes, condensed naphthalenes, sulfosuccinates and/or derivatives thereof, tridecyl and/or dodecyl benzene sulfonic acids, mixtures of two or more thereof, and the like. The surfactant may include $C_9$-$C_{11}$ Pareth 8 (a polyethylene glycol ether of a mixture of $C_9$-$C_{11}$ fatty alcohols with an average of 8 moles of ethylene oxide), $C_{11}C_{15}$ Pareth 3 (a polyethylene glycol ether of a mixture of $C_{11}C_{15}$ alcohols with an average of 3 moles of ethylene oxide), Meroxapol 252 (oxirane), octyl betaine, polyethylene glycol cocoamine, or a mixture of two or more thereof. The surfactant may comprise one or more antifoam agents (e.g., potassium hydroxide, octyl diproprionate), foam enhancing agents, oil removal agents (e.g., potassium hydroxide, sodium borate), rheology modification (thinning) agents (e.g., polyacrylic acid), penetration agents (e.g., propylene glycol), rinse aids, or a mixture of two or more thereof. The concentration of the surfactant in the supplemental medium (B) may be in the range up to about 25% by weight, or from about 1 to about 25% by weight, or from about 5 to about 15% by weight. These concentrations may be suitable for sale as concentrates and, optionally, for use in the inventive cleaning and disinfecting process. These concentrations may be diluted with water prior to or during use.

The supplemental medium (B) may further comprise one or more scale inhibitors, stabilizers (e.g., lauramine oxide), preservatives (e.g., DMDM Hydantoin, an antimicrobial formaldehyde releaser preservative (CAS number 6440-58-0) available from Lonza), defloculents or suspension agents (e.g., polyacrylic acid-sodium salt), metal passivators, thickening agents (e.g., lauramine oxide, hydroxyethylcellulose, propylene glycol, or a mixture of two or more thereof), tonicity adjusting agents (e.g., sodium chloride, potassium chloride, glucose), or a mixture of two or more thereof. The concentrations of each of these may be in the range up to about 25% by weight, or from about 0.1 to about 10% by weight, or from about 0.1 to about 5% by weight. These concentrations may be diluted with water prior to or during use.

The volumetric ratio of the disinfectant medium (A) to the supplemental medium (B) that may be used in the cleaning and/or disinfecting steps of the inventive process may be in the range from about 5:1 to about 1:5, or from about 4:1 to about 1:4, or from about 3:1 to about 1:3, or from about 2:1 to about 1:2, or from about 1.5:1 to about 1:1.5, or about 1:1.

The pH of the disinfectant medium (A) may be in the range from about 1 to about 8, or from about 3 to about 6. The pH of the supplemental medium (B) may be in the range from about 6 to about 14, or from about 6 to about 9. The pH of the disinfectant medium (A) and/or the supplemental medium (B) may be adjusted using sodium or potassium hydroxide, triethanol amine, citric acid, or a mixture of two or more thereof.

As indicated, above, when used in the inventive cleaning and disinfecting process, the disinfectant medium (A) and the supplemental medium (B) may be used at the indicated concentrate concentrations, or they may be diluted with water. The dilution of the disinfectant medium (A) may be up to 1000 parts by volume of water per part by volume of the disinfectant medium (A) (i.e., up to about 1000:1), or from about 20:1 to about 1000:1, or from about 35:1 to about 500:1; or from about 50:1 to about 250:1. Similarly, the dilution of the supplemental medium (B) may be up about 1000 parts by volume of water per part by volume of the supplemental medium (B), or from about 20:1 to about 1000:1, or from about 35:1 to about 500:1; or from about 50:1 to about 250:1.

The two-part liquid cleaning and disinfecting compositions made from the disinfectant medium (A) and the supplemental medium (B) may be used in a process for cleaning and disinfecting a substrate (or article), including a process for cleaning and disinfecting a substrate that cannot withstand the high temperatures required for steam sterilization.

The process may be a one-step process for cleaning and disinfecting the substrate, or a two-step process for cleaning and disinfecting the substrate. The process may include a manual pre-cleaning step.

The one-step process may comprise contacting the substrate with the supplemental medium (B) and the disinfectant medium (A) for an effective period of time to clean and disinfect the substrate. This process may be conducted at a temperature in the range from about 15° C. to about 60° C., or from about 18° C. to about 60° C., or from about 18° C. to about 56° C., or from about 18° C. to about 50° C., or from about 18° C. to about 40° C., or from about 18° C. to about 30° C., or from about 18° C. to about 24° C. The contacting time may be in the range from about 0.5 to about 240 minutes, or from about 2 to about 60 minutes.

The two-step process may comprise (1) contacting the substrate with the supplemental medium (B) to clean the substrate; and (2) contacting the substrate with the disinfectant medium (A) to disinfect the substrate. The process may comprise (1) contacting the substrate with the supplemental medium (B) and the disinfectant medium (A) to clean the substrate, and (2) contacting the substrate with the disinfectant medium (A) to disinfect the substrate. The process may comprise (1) contacting the substrate with the supplemental medium (B) to clean the substrate, and (2) contacting the substrate with the disinfectant medium (A) and the supplemental medium (B) to disinfect the substrate. The process may comprise (1) contacting the substrate with the supplemental medium (B) and the disinfectant (A) to clean the substrate, and (2) contacting the substrate with the disinfectant medium (A) and the supplemental medium (B) to disinfect the substrate. The two-step process may optionally include the step of rinsing the substrate between process steps (1) and (2).

The temperature used during each of steps (1) and (2) may be in the range from about 15° C. to about 60° C., or from about 18° C. to about 60° C., or from about 18° C. to about 56° C., or from about 18° C. to about 50° C., or from about 18° C. to about 40° C., or from about 18° C. to about 30° C., or from about 18° C. to about 24° C. Each of steps (1) and (2) may be conducted at room temperature.

The contacting time for each of the steps (1) and (2) may be for a period of time in the range from about 0.5 to about 240 minutes, or from about 0.5 to about 60 minutes, or from about 0.5 to about 10 minutes, or about 2 to about 8 minutes, or about 4 to about 8 minutes, or about 6 minutes.

The substrates that may be cleaned and disinfected may include medical, dental, pharmaceutical, veterinary or mortuary instruments and devices. These may include endoscopes. The substrates may be made of a material comprising brass, copper, aluminum, stainless steel, carbon steel, plastic, glass, adhesive, or a combination of two or more thereof.

In the field of medical practice many diagnostic, therapeutic or surgical procedures are performed using endoscopes. Endoscopes fall into two large categories, rigid or flexible, depending upon their construction and how they are intended to be used. Whereas rigid endoscopes tend to be constructed of metallic components, flexible endoscopes are generally constructed of polymeric materials. In many cases both metallic and polymeric materials are used. In either case, these medical devices may further comprise fiber optic, electronic or other features that make them both expensive and delicate with respect to their handling; especially after their intended use when these instruments are being cleaned and disinfected for subsequent use.

This handling generally involves a combination of post procedure wipe down, manual pre-cleaning in a sink, and disinfection or sterilization depending upon the type of endoscope and the type of procedure in which it will be used.

Substrates that contact blood, for example, endoscopes, are usually sterilized before their next use. For other substrates or devices, high level disinfection (HLD) may be sufficient. The difference between high level disinfection and sterilization is generally related to the potency of the sterilizing medium used, its mode of action and the duration of exposure.

The disinfecting or sterilizing medium for many medical devices may be steam, a vaporous chemistry (e.g. vaporous hydrogen peroxide or ethylene oxide) or a liquid chemistry. However, for many sophisticated devices, such as various endoscopes and the like, steam cannot be safely used because many of these devices are sensitive to, and can be destroyed by, exposure to high heat. Similarly, other media may introduce other contraindications including time consuming steps (e.g. out gassing after exposure to ethylene oxide) or labor intensive preparatory steps (extensive cleaning and drying prior to exposure to vaporous hydrogen peroxide, and inability to reach into long and narrow area of lumens because of no active flow of gas). This invention provides an alternative wherein low temperature liquid reprocessing of heat sensitive devices such as endoscopes may be used in order to achieve cleaning and disinfection. Whether for use in disinfection or sterilization, the medium used will typically be established as a sterilant, meaning that at a given concentration and time the medium can kill greater than 6 logs of the most resistant organism for that particular medium. The achievement of a 6 log reduction is what is needed to obtain a sterilant designation. Disinfection, while often using the same sterilant medium as in sterilization, may be performed at a lower concentration or for a shorter period of time (or both) in order to achieve the appropriate level of disinfection for the intended use of some devices.

The cleaning and disinfecting process that may be used for an endoscope may start with a manual, post procedural wipe down. That process can then be extended to a manual pre-cleaning step and a manual disinfection step, in that order. This may represent the least costly alternative to endoscope reprocessing but generally requires a longer exposure time in the disinfectant and can expose the user to greater risk of contact with the chemistries used, or to the contaminated devices themselves. This process represents the most commonly used, but diminishing method for cleaning and disinfecting endoscopes.

At the other end of the spectrum, fully automated machines (reprocessors) are available that eliminate most of the manual steps. These automated systems have often been co-developed and co-validated along with a specific disinfectant chemistry to provide a fully integrated reprocessing method. These fully automated machines and their dedicated disinfectant chemistries are also the most expensive alternative and represent a substantially smaller portion of the overall reprocessing procedures being performed.

In recent years, a number of "open" reprocessors have been introduced to the marketplace for cleaning and disinfecting endoscopes. While they may automate many, if not all, of the steps associated with manual reprocessing of endoscopes, they generally are not co-developed with a specific disinfectant chemistry formulation but are intended to be used with one or more pre-existing chemistries. These machines are flexible in that they may be used with a variety of disinfectants including aldehydes, peroxides and peracetic acid based chemistries. These devices may provide an alternative that combines semi-automated processing with a broader range of available chemistries than is available with the fully integrated systems. And, although somewhat more expensive than manual methods, these open systems are growing with respect to the number of processes being performed.

While the fully automated systems may provide a more controlled approach than the other methods, the open systems may have a broader scope of available chemistries to choose from. This can be important because each endoscope may react differently to a particular chemistry. That is, a particular endoscope may be more susceptible to damage when using one chemistry than another. Often the decision as to which fully automated system to buy is based on the particular endoscopes the buyer uses and whether the dedicated chemistry that is exclusively used in that system is compatible for use with the endoscopes that will be treated.

An advantage of the present invention is that the inventive two-part liquid cleaning and disinfecting composition may be used in a dedicated system or it can be adapted for use in a manual or an open system. The inventive two-part liquid composition can be used to support and perform either high level disinfection or sterilization in the same system. The inventive two-part liquid composition can be used with a broad combination of endoscopes and is capable of being easily adapted to the particular needs of a given endoscope.

The inventive two-part liquid composition allows automated dispensing and reduces the exposure of the user to contact with the sterilants where mixtures or dilutions are manually prepared as in static soak methods.

The disinfecting medium (A) and the supplemental medium (B) may be kept in separate containers prior to use to increase their stability and to prevent ingredients from interacting with one another in ways that may decrease their potency or possibly introduce unwanted side reaction products.

In the reprocessing sequence described above, cleaning precedes disinfection. This convention is notable in that the operating firmware of many reprocessors addresses each of these operations as individual steps that are separated by at least one optional rinsing cycle.

The inventive cleaning and disinfecting process may be conducted using any suitable cleaning and disinfecting apparatus. Examples of these are disclosed in U.S. Pat. Nos. 5,077,008; 8,530,184 B2; and 8,691,562 B2; and in U.S. Patent Publication US 2012/0230870 A1.

The two-step cleaning and disinfecting processes using the disinfectant medium (A) and the supplemental medium (B) may be conducted using the apparatus schematically illustrated in FIG. 1. Referring to FIG. 1, the apparatus includes a basin 10 for containing the substrate (e.g., endoscope) to be cleaned and disinfected, a tank or vessel 12 for containing the disinfectant medium (A) (Part A as shown in the drawing), a separate tank or vessel 14 for the supplemental medium (B) (Part B as shown in the drawing), piping or tubing for connecting the tanks or vessels 12 and 14 to basin 10, a water supply 16 for adding water to the basin 10, valve 18 for controlling the flow of water from the water supply 16 to the basin 10, valve 20 for controlling the flow of fluid out of the basin 10 to drain 21, dosing pump 22 for controlling the flow of the disinfectant medium (A) to the basin 10, dosing pump 24 for controlling the flow of the supplemental medium (B) to the basin 10, and controller 26, which can be a microprocessor, for controlling valves 18 and 20, a heater (not shown) and dosing pumps 22 and 24.

Figure 2:
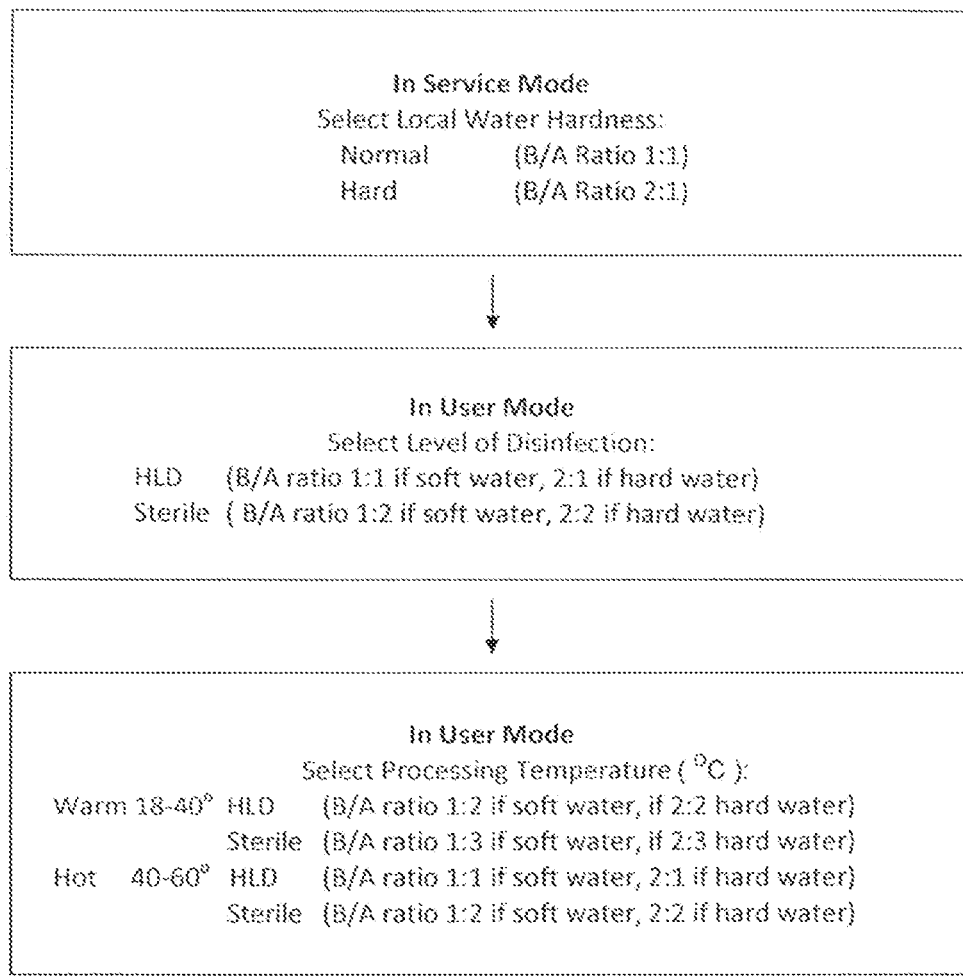
FIG. 2 is a flow sheet showing operational steps and exemplary process conditions for using the apparatus illustrated in FIG. 1.

Alternative service modes for operating the apparatus illustrated in FIG. 1 are exemplified in FIG. 2. The B/A ratios shown in FIG. 2 are volumetric ratios for the ratio of the supplemental medium (B) to the disinfectant medium (A). The terms "soft" and "hard" water used in FIG. 2 are terms of art referring to the concentration of calcium carbonate in the water. For purposes of this disclosure, the classifications used by the U.S. Geological Services for what constitutes soft and hard water are used herein. The US Geological Services classifies water with 0-60 mg/L of calcium carbonate as 'soft', or at 61-120 mg/L as 'moderately hard', or at 121-180 mg/L as 'hard', and at more than 180 mg/L as 'very hard.'

In the examples provided below, the disinfectant medium (A) contains 65% by weight water and 35% by weight peracetic acid (PAA). The supplemental medium (B) contains 3% by weight triethanol amine, 2.2% by weight ethanol amine, 2% by weight polyalkylene glycol, 3% by weight octyldimethylamine oxide, 4% by weight Alcalase Ultra 2.5 L, 4% by weight Savinase 16 L Type EX, 1% by weight tolyltriazole, 1% by weight corrosion inhibitor, 3% by weight citric acid, 1.1% by weight oxirane, 2% by weight polyethylene glycol cocoamine, 20% by weight propylene glycol, 0.005% by weight anti-foam agent, 0.15% by weight calcium chloride, 0.0125% by weight fragrance, with the remainder being soft water. In the following examples the B/A ratios are volumetric ratios.

Example 1

A cleaning and disinfection process is conducted using the supplemental medium (B) in a first cleaning step, and then a combination of parts (A) and (B) in a second disinfection step. Four different options are used for the disinfection step. Both the cleaning and disinfecting steps are conducted at room temperature. The ratio of (B) to (A) is adjusted in response to the hardness of the water that is used.

| Step | Ratio B/A | System Vol. | Vol. Part (B) | Vol. Part (A) | Final [PAA] Conc. | Comments/parameters |
|---|---|---|---|---|---|---|
| Cleaning | 1:0 | 17 liters | 80 mLs | 0.0 mls | 0.0 ppm | ≤150 mg/L hardness |
| Disinfection Option 1 | 1:1 | 17 liters | 80 mLs | 80 mLs | ~2,570 ppm | ≤150 mg/L hardness |
| Disinfection Option 2 | 2:1 | 17 liters | 160 mLs | 80 mLs | ~2,570 ppm | ≤300 mg/L hardness |

-continued

| Step | Ratio B/A | System Vol. | Vol. Part (B) | Vol. Part (A) | Final [PAA] Conc. | Comments/parameters |
|---|---|---|---|---|---|---|
| Disinfection Option 3 | 3:1 | 17 liters | 240 mLs | 80 mLs | ~2,570 ppm | ≤450 mg/L hardness |
| Disinfection Option 4 | 4:1 | 17 liters | 320 mLs | 80 mLs | ~2,400 ppm* | ≤600 mg/L hardness |

This example shows that by altering the proportion of part (B) used during disinfection, the user can use the hardness control components of part (B) to adjust for the local water hardness.

Example 2

The inventive two-part liquid composition may be used in traditional automated endoscope reprocessor (AER) disinfections. Combining part (B) with water produces a cleaning solution for use during the separate cleaning phases controlled by existing firmware in the AER. This requires no modification of any operational steps by the user or operating system software and part (B) is only 'seen' as a cleaner by the processor's control system. Following this step, and allowing the system to perform its traditional, but in this application unnecessary rinsing cycle, the parts (A) and (B) are used together as a disinfection solution. No changes to existing procedures or programming steps are required. The use of part (B) replaces the traditional builders of the disinfecting solutions used in the prior art saving on costs and complexity. This configuration also allows the user to circumvent the rinsing phase (if software allows) saving time and utility costs as a further benefit. In this example, standard AER operations, cleaning followed by draining and then disinfection are used.

| Step | Ratio B/A | System Vol. | Vol. Part (B) | Vol. Part (A) | Final [PAA] Conc. | Comments/parameters |
|---|---|---|---|---|---|---|
| Cleaning | 1:0 | 17 liters | 80 mLs | 0.0 mLs | 0.0 ppm | 50° C.* operations, water ≤150 mg/L, corrosion resistant devices |
| Disinfection | 1:1 | 17 liters | 80 mLs | 80 mLs | ~2,400 ppm | 50° C.* operations, water ≤150 mg/L, corrosion resistant devices |

Because part (B) is used in the disinfection step, a rinsing step is not required. The cleaning solution is drained and the disinfection solution is then used.

Example 3

For disinfection or sterilization of a medical device to be successful, an effective cleaning of the medical device is required. The cleaning step can be performed using part (B), or part (B) in combination with part (A). After the required cleaning step, which may be performed manually or with the aid of a different cleaning apparatus, parts (A) and (B) can be used for high level disinfection or sterilization in a process that has been adapted to the temperature sensitive requirements of certain endoscopes. Although disinfection in the chemistries of the present invention is conceptually described to be used in convenient 1:1 proportions (e.g. 80 mLs each of parts (B) and (A)) the relative proportions can be adjusted in different ways to achieve different disinfection use dilution conditions. For purposes of illustration, a 1:1 ratio is set as desirable for a use in a disinfection operation performed at 50° C. If a particular endoscope is unusually sensitive to the heat of traditional low temperature disinfection or sterilization procedures (e.g. 50° C.) the ratio of part (B) to part (A) can be tailored such that lower temperatures can be used while maintaining disinfection efficacy. This is also desirable when a nominal 50° C. disinfecting temperature cannot be reached. A 1:1.2 ratio of part (B) to part (A) can be used at a lower temperature (40° C.) providing more steriliant to offset the impact on microbial efficacy that the reduction in heat might cause. A 1:1.5 ratio can be used at 30° C. and if the desired operating conditions are room temperature (e.g. 20° C.) a 1:2 ratio can be used for example.

If this much of part (A) introduces too much corrosion for a particularly sensitive device to withstand multiple disinfection cycles, the proportions can be adjusted to 2:1.5 or 2:2.0 thereby increasing the amount corrosion control provided by part (B) in order to reduce corrosion while still providing the extra disinfectant quantity used to offset the lower temperatures (See also Example 4).

| Step | Ratio B/A | System Vol. | Vol. Part (B) | Vol. Part (A) | Final [PAA] Conc. | Comments/parameters |
|---|---|---|---|---|---|---|
| Disinfection Option 1 | 1:1.0 | 17 liters | 80 mLs | 80 mLs | ~2,400 ppm | 50° C. operations, water ≤150 mg/L, corrosion resistant devices |
| Disinfection Option 2 | 1:1.2 | 17 liters | 80 mLs | 96 mLs | ~3150 ppm | 40° C. operations, water ≤150 mg/L, corrosion resistant devices |
| Disinfection Option 3 | 1:1.5 | 17 liters | 80 mLs | 120 mLs | ~3,850 ppm | 30° C. operations, water ≤150 mg/L, corrosion resistant devices |
| Disinfection Option 4 | 1:2.0 | 17 liters | 80 mLs | 160 mLs | ~4,100 ppm | 20° C. operations, water ≤150 mg/L, corrosion resistant devices |

This example shows that the operator has a choice of temperatures that can be used while maintaining disinfection efficacy and adequate water hardness control. By increasing the proportion of part (A) that is used, it is possible to select a lower temperature to achieve the desired kill in less time than by extending exposure.

Example 4

Parts (A) and (B) can be used for treating corrosion sensitive endoscopes. If a device is not particularly sensitive to heat but is constructed of highly corrosion sensitive materials, the ratio of part (B) to part (A) can be adjusted such that the proper amount of part (A) is used but a larger amount of part (B) is added, for example in a ratio of 2:1 or 3:1. This provides more part (B) to offset corrosion.

| Step | Ratio B/A | System Vol. | Vol. Part (B) | Vol. Part (A) | Final [PAA] Conc. | Comments/parameters |
|---|---|---|---|---|---|---|
| Disinfection | 1:1 | 17 liters | 80 mLs | 80 mLs | ~2,400 ppm | 50° C. operations, water ≤150 mg/L hardness, or devices not normally sensitive to corrosion |
| Disinfection | 2:1 | 17 liters | 160 mLs | 80 mLs | ~2,400 ppm | 50° C. operations, water ≤300 mg/L hardness, or devices somewhat sensitive to corrosion |
| Disinfection | 3:1 | 17 liters | 240 mLs | 80 mLs | ~2,100 ppm | 50° C. operations, water ≤450 mg/L hardness, or devices highly sensitive to corrosion |

This example shows that by increasing the proportion of part (B) that is used, it is possible to provide extra corrosion resistance while maintaining the level of part (A) needed to generate an effective kill. This can be applied to the Example 3 options discussed above or whenever the use of more part (A) is indicated or desired.

Example 5

Parts (A) and (B) can be used together in the ratios exemplified below for difficult to disinfect endoscopes. If a device is not particularly heat sensitive but has a history of being resistant to standard levels of disinfectant (e.g. is constructed of particular materials or of a particularly complex design that protects contaminating organisms from effective exposure to the disinfectant), the ratio of part (B) to part (A) can be adjusted to 1:2 or 2:2 depending on sensitivity to corrosion and processed at the higher traditional temperatures.

| Step | Ratio B/A | System Vol. | Vol. Part (B) | Vol. Part (A) | Final [PAA] Conc. | Comments/parameters |
|---|---|---|---|---|---|---|
| Disinfection | 1:2 | 17 liters | 80 mLs | 160 mLs | ~3,900 ppm | 50° C. operations, water ≤150 mg/L hard, or devices not normally sensitive to corrosion |

-continued

| Step | Ratio B/A | System Vol. | Vol. Part (B) | Vol. Part (A) | Final [PAA] Conc. | Comments/parameters |
|---|---|---|---|---|---|---|
| Disinfection | 2:2 | 17 liters | 160 mLs | 160 mLs | ~3,900 ppm | 50° C. operations, water ≤300 mg/L hard, or devices somewhat sensitive to corrosion |

This example shows that by increasing (doubling) the quantity of part (A) that is used, the likelihood of generating an efficacious kill when starting with a difficult to disinfect device can be achieved. The use of part (B) can be adjusted accordingly as well.

In the following Examples 6-8, parts (A) and (B) are as described above for Examples 1-5. Builders 1 contains two sodium phosphates, benzotriazole, tetrasodium ethylene diamine tetraacetate, a sodium molybdate, sodium hydroxide, an ethoxylated polyoxypropylene, a polyacrylate, a sodium phosphate, and water. Builders 2 contains a sodium phosphate, a sodium benzotriazole and a sodium salt of ethylene diamine tetraacetic acid.

Example 6

Figure 3A:
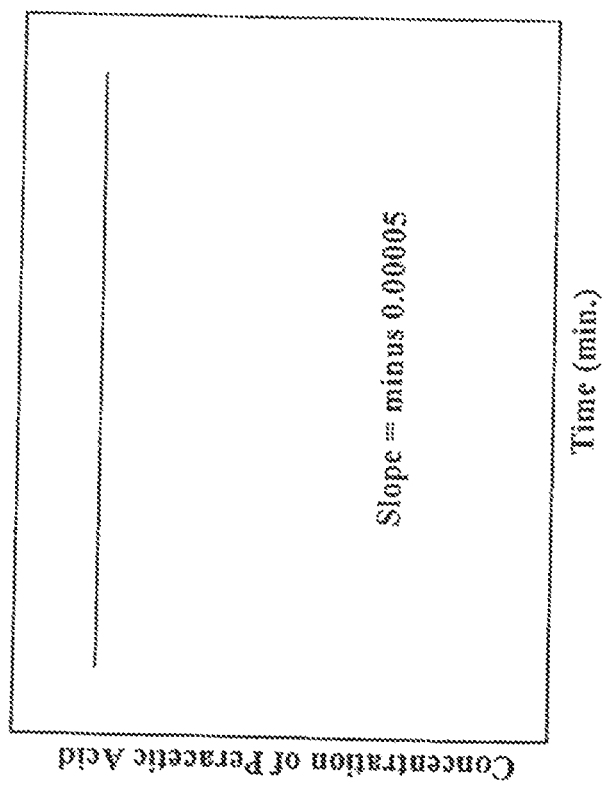
FIGS. 3A-3D are graphs that show the stability of peracetic acid over the time required for a single disinfection cycle as a function of the presence or absence of two different builders formulations as well as the supplemental medium (B) of the present invention.
Figure 3B:
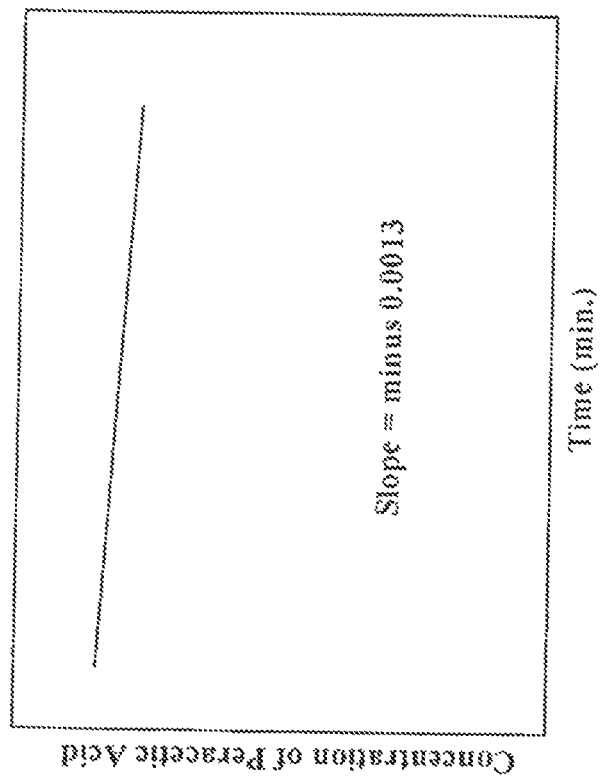
Figure 3D:
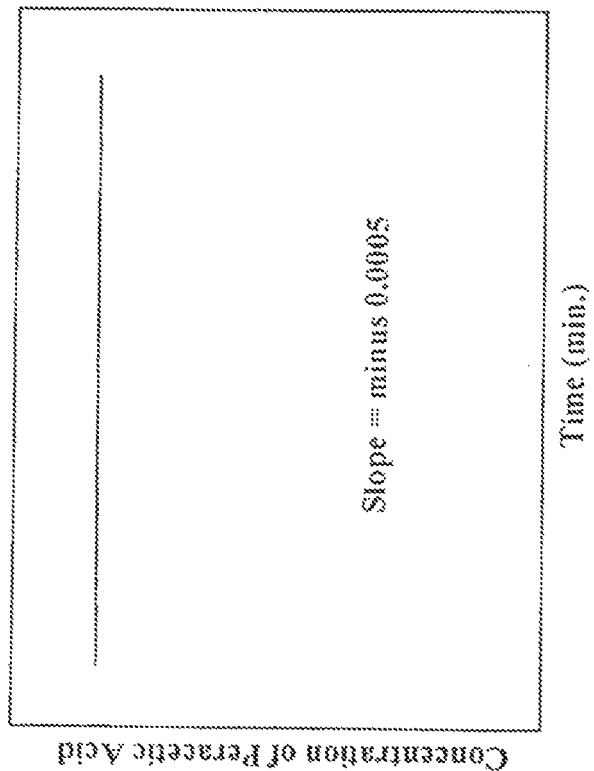
Figure 3C:
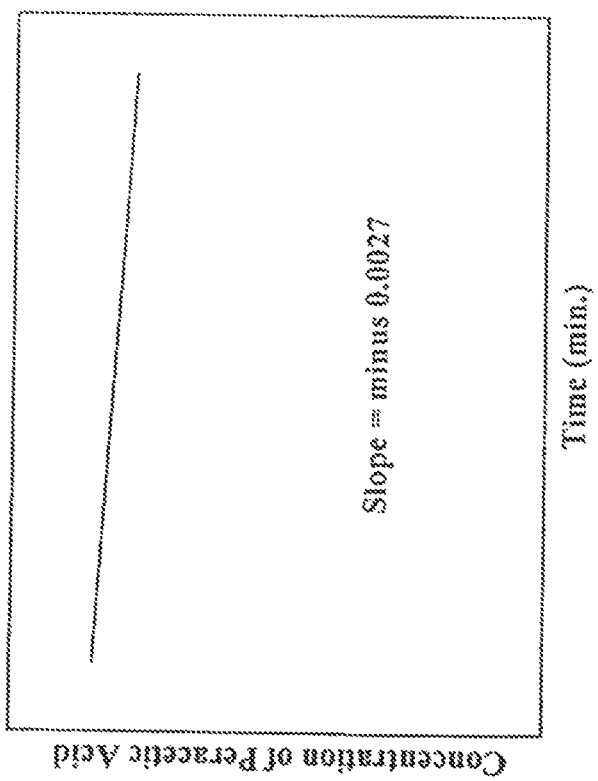

FIGS. 3A-3D show the stability of peracetic acid over the time required for a single disinfection cycle (short term stability) when used alone (FIG. 3A), or in combination with the prior art Builders 1 (FIG. 3B), and Builders 2 (FIG. 3C) or in the supplemental medium part (B) of the invention (FIG. 3D). The slopes can be used to understand the kinetics of stability (or conversely, the nature of degradation in PAA). Whereas, a slope of 0 (horizontal flat line) indicates perfect stability over the time range studied; and a slope of minus 1 indicates immediate degradation, the slope of minus 0.00005 (FIG. 3A) indicates that the PAA solution is stable by itself over the indicated time scale. However, a slope of minus 0.0013 (FIG. 3B) is indicative of the somewhat relatively rapid degradation of PAA caused by ingredients in the exemplified Builders 1. The minus 0.0027 slope of FIG. 3C shows that the PAA component in this combination is nearly at the same level as in the case for FIG. 3B. The impact of the supplemental medium part (B) of the present invention (FIG. 3D) shows a slope of minus 0.0005 demonstrating that this supplemental medium part (B) returns the stability of the PAA component to nearly the same level as in the case for pure PAA as shown in FIG. 3A.

Example 7

Figure 4B:
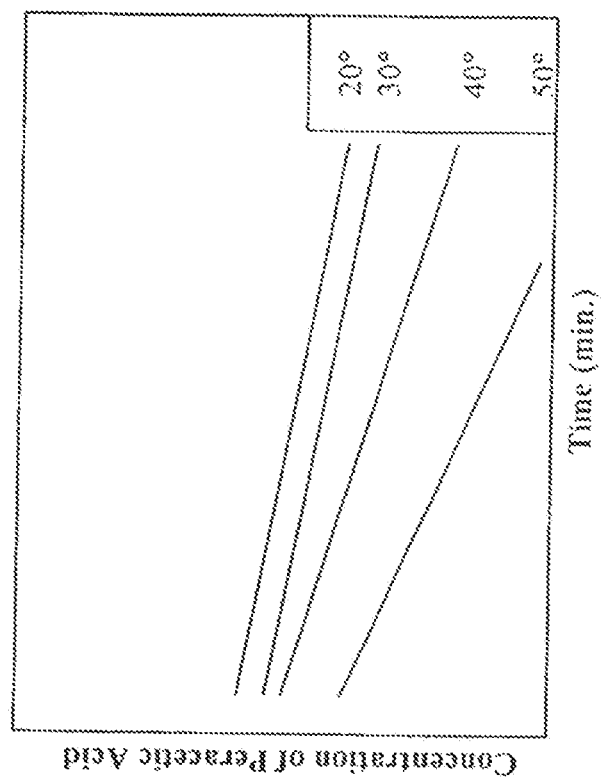
FIGS. 4A-4D are graphs that show the stability of peracetic acid over the time required for a single disinfection cycle, at different disinfection solution temperatures, and as a function of the presence or absence of two different builders formulations as well as the supplemental medium (B) of the present invention.
Figure 4A:
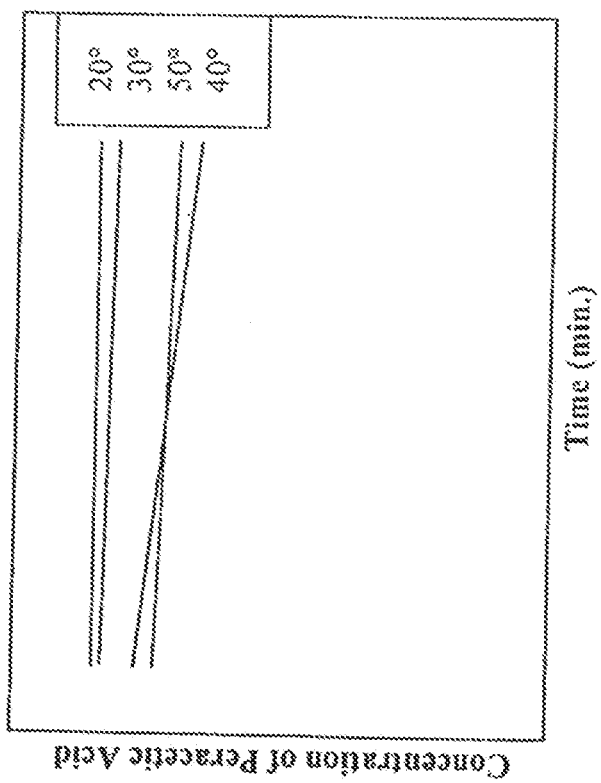
Figure 4D:
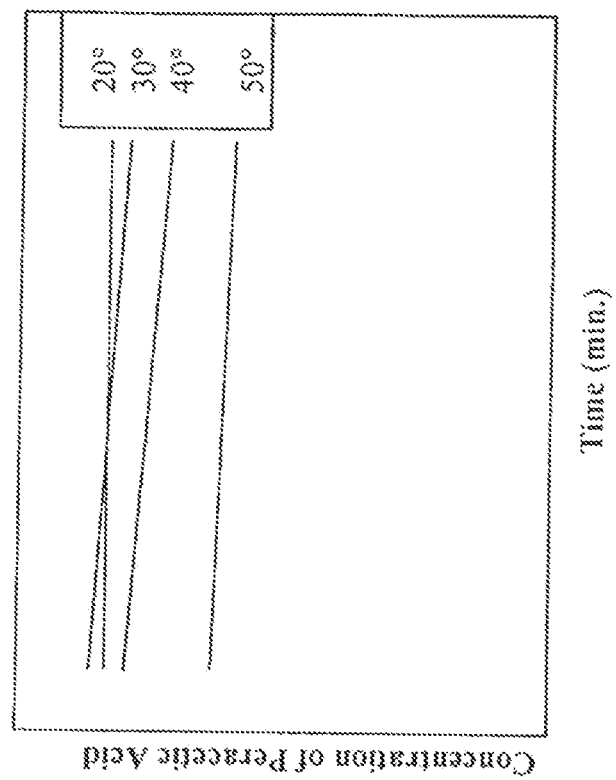
Figure 4C:
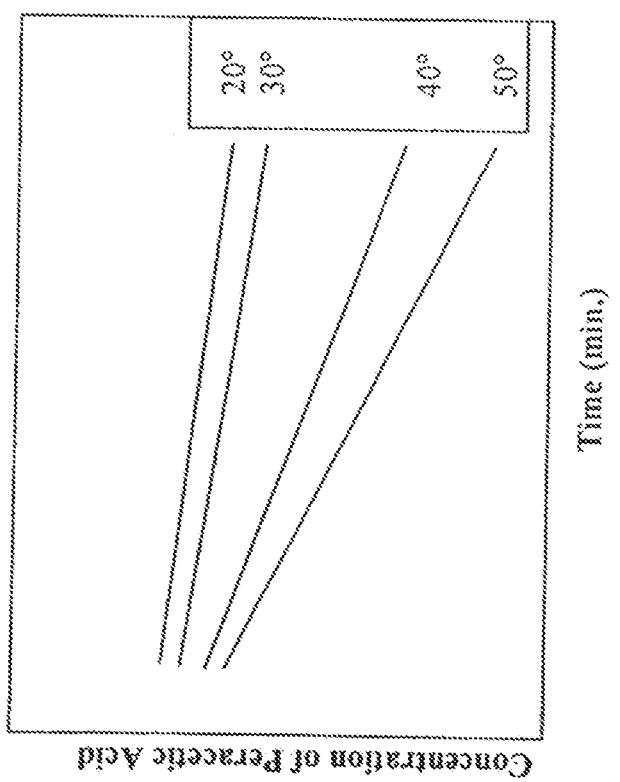

FIGS. 4A-4D show the stability of peracetic acid over the time required for a single disinfection cycle (stability), at different disinfection solution temperatures when used alone (FIG. 4A), or in combination with prior art Builders 1 (FIG. 4B) or Builders 2 (FIG. 4C) or the supplemental medium part (B) of the present invention (FIG. 4D). The trend of each line can be used to understand the kinetics of stability (or conversely, the rate and amount of degradation of PAA). The trends of the lines in FIG. 4A indicates good stability at the lower temperatures, but the solution concentration is lowered and there is less stability as temperature increases over the time range studied. The PAA solution is relatively stable when used alone (FIG. 4A) although this condition does not provide the required buffering, anti-corrosion or chelating capacities provided by builders. FIGS. 4B and 4C show considerable change in both the initial solution concentration and the subsequent rate of degradation of PAA as the temperature of the solution increases when using prior art builders. FIG. 4B is indicative of a rapid degradation caused by ingredients in Builders 1. The PAA solution is relatively unstable in the presence of Builders 1 and Builders 2. FIG. 4D shows PAA solution stability similar to the stability shown in FIG. 4A. Concentrations are nearly the same level as in FIG. 4A when using the builders of the present invention. The impact of supplemental medium part (B) of the present invention (FIG. 4D) demonstrates that the stability for this solution is nearly the same as in the case for pure PAA as shown in FIG. 4A, but with the additional benefits of the buffering, anti-corrosion and chelating capacities provided by part (B) Both initial and endpoint concentrations are higher in both FIGS. 4A and 4D.

Example 8

Figure 5B:
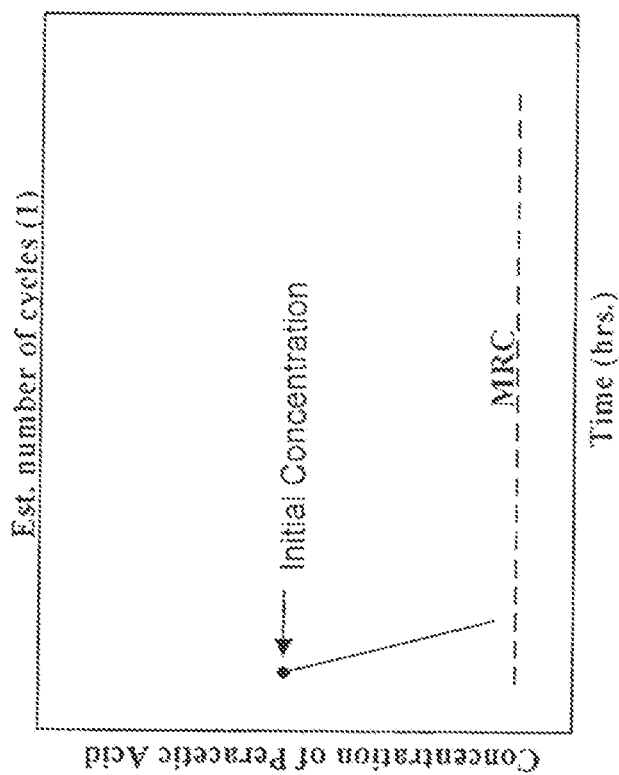
FIGS. 5A-5D are graphs that show the stability of peracetic acid both initially and over the time required for multiple disinfection cycles as a function of the presence or absence of two different builders used as well as the supplemental medium (B) of the present invention.
Figure 5A:
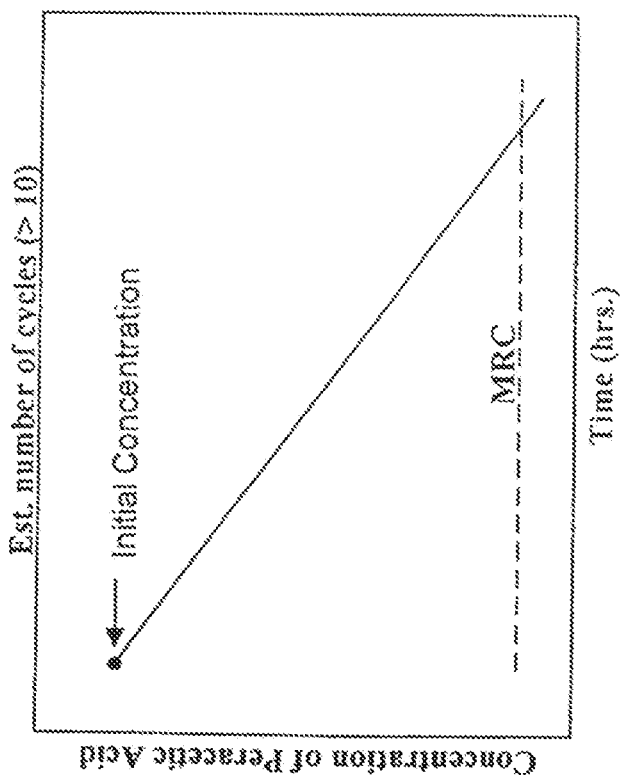
Figure 5D:
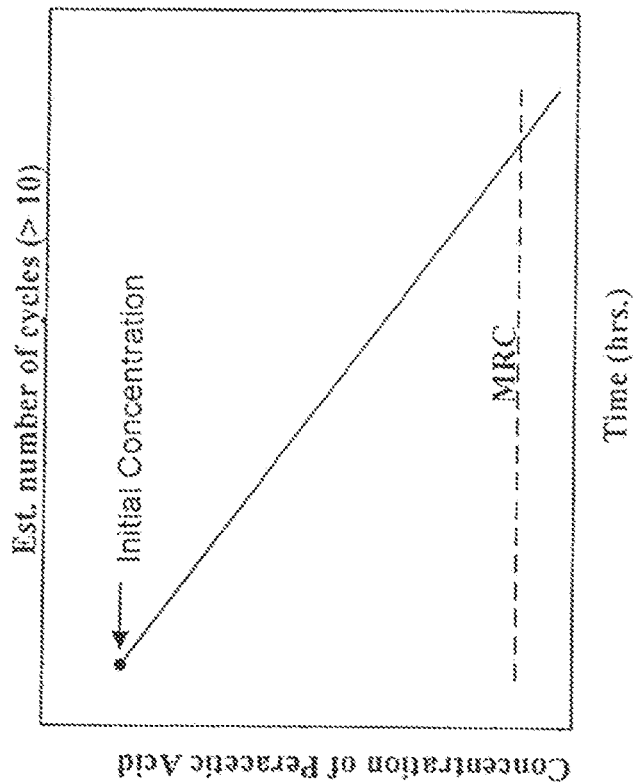
Figure 5C:
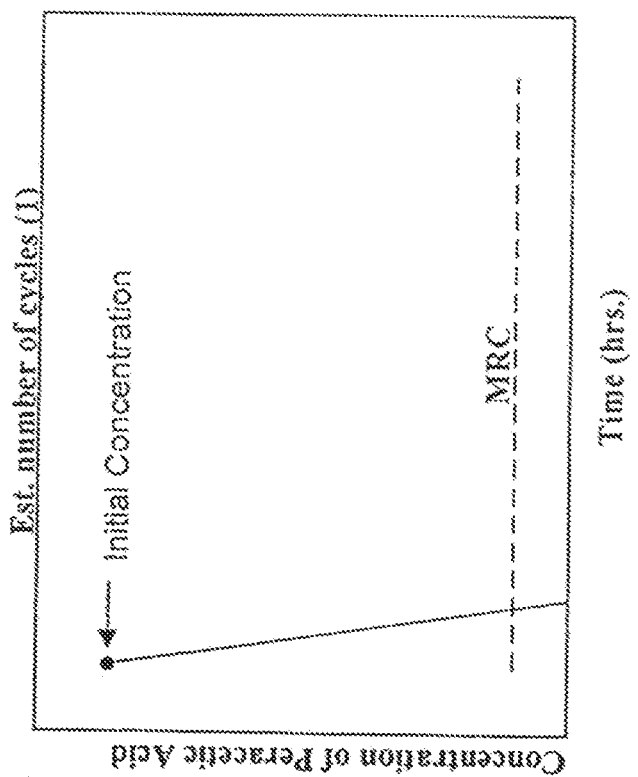

FIGS. 5A-5D show the stability of peracetic acid both initially and over the time required for multiple disinfection cycles (stability) when used alone (FIG. 5A), or in combination with Builders 1 of the prior art (FIG. 5B), Builders 2 of the prior art (FIG. 5C) or the supplemental medium part (B) of the present invention (FIG. 5D). In a desirable embodiment, the stability of the inventive composition would be such that it could support more than one cycle before needing to be replenished. To do this requires sufficient stability so that the resulting disinfection solution concentration will be high enough to be above the recommended minimum concentration for disinfection/sterilization in each cycle performed. While the actual exposure time for disinfection/sterilization may only be, for example, 5-7 minutes, each cycle can take from 30-45 minutes to complete all the other steps in the process and thus the number of cycles that can be performed depends on the overall stability of each solution made over the total time during and between all operations. For this data, a one hour cycle time is used for the calculation. In the experiments that give the data for FIG. 5A, peracetic acid alone, up to 10 complete hour long cycles are possible. However, none of the benefits of a builders would occur FIGS. 5B and 5C show that only one cycle can be run. The experiments that give the data for FIG. 5D indicate that the supplemental medium part (B) of the present invention matches or exceeds the performance seen for pure PAA thus enabling up to 10 cycles to be performed over 10 hours, and all the benefits of using the supplemental medium (B) are realized as well. It should also be noted that while the prior art Builders 2 (FIG. 5C) has as high an initial concentration as PAA alone (FIG. 5A) so does the present invention using part (B) as can be seen in FIG. 5D.

While the invention has been explained in relation to various embodiments, it is to be understood that modifications thereof may become apparent to those skilled in the art upon reading the specification. Therefore, it is to be understood that the scope of the invention specified herein is intended to include all modifications that may fall within the scope of the appended claims.

The invention claimed is:

1. A two-part liquid composition for cleaning and disinfecting a substrate contaminated with living microorganisms, comprising:
   (A) a disinfectant medium comprising water; peracetic acid, acetic acid, hydrogen peroxide and sulfuric acid, wherein the concentration of peracetic acid in the disinfectant medium (A) is from about 5 to about 60% by weight, the concentration of sulfuric acid in the disinfectant medium (A) is from about 0.5% to about 2% by weight, and the pH of the disinfectant medium (A) being from about 1 to about 8; and
   (B) a supplemental medium comprising water, an enzymatic cleaner, a non-enzymatic cleaner, a corrosion inhibitor, a surfactant and a chelator; wherein the enzymatic cleaner comprises a protein digesting enzyme; and wherein the non-enzymatic cleaner comprises an alkanol amine, a polyalkylene glycol, an alkyl diproprionate, an alkyl dialkylamine oxide, or a mixture of two or more thereof, wherein the concentration of the enzymatic cleaner in (B) is from about 0.2 to about 25% by weight, the concentration of the non-enzymatic cleaner in (B) is from about 0.1 to about 25% by weight, the concentration of the corrosion inhibitor in (B) is from about 1% to about 10% by weight, the concentration of the surfactant in (B) is from about 1 to about 25% by weight, the concentration of the chelator in (B) is from about 0.1 to about 70%, the pH of the supplemental medium (B) is from about 6 to about 14, and the volumetric ratio of (A) to (B) is in the range from about 5:1 to 1:5.

2. The composition of claim 1 wherein the disinfectant medium (A) comprises from about 15% to about 45% by weight of peracetic acid.

3. The composition of claim 1 wherein supplemental medium (B) further comprises a buffer, a pH modifier or a mixture thereof.

4. The composition of claim 1 wherein the alkanol amine comprises monoethanol amine, diethanol amine, triethanol amine, or a mixture of two or more thereof.

5. The composition of claim 1 wherein the alkyl diproprionate comprises an octyl diproprionate.

6. The composition of claim 1 wherein the alkyl dialkylamine oxide comprises octyl dimethylamine oxide.

7. The composition of claim 1 wherein the supplemental medium (B) comprises monoethanolamine, triethanolamine, octyldimethylamine oxide, a polyalkylene glycol, octyl dipropionate, or a mixture of two or more thereof.

8. The composition of claim 1 wherein the supplemental medium (B) comprises from about 1 to about 25% by weight of the non-enzymatic cleaner.

9. The composition of claim 1 wherein the supplemental medium (B) comprises from about 0.5 to about 10% by weight of the enzymatic cleaner.

10. The composition of claim 3 wherein the buffer comprises an alkali metal phosphate, an alkali metal carbonate, or a mixture thereof.

11. The composition of claim 3 wherein the supplemental medium (B) comprises up to about 15% by weight of the buffer.

12. The composition of claim 1 wherein the supplemental medium (B) comprises from about 1% to about 5% by weight of the corrosion inhibitor.

13. The composition of claim 1 wherein the supplemental medium (B) comprises from about 0.3 to about 60% by weight of the chelator.

14. The composition of claim 1 wherein the surfactant comprises a detergent, wetting agent, emulsifier, foaming agent and/or dispersant.

15. The composition of claim 1 wherein the surfactant comprises a compound that contains at least one hydrophobic group and at least one hydrophilic group.

16. The composition of claim 1 wherein the surfactant comprises a water insoluble component and a water soluble component.

17. The composition of claim 1 wherein the surfactant comprises an anionic, cationic, zwitterionic and/or nonionic compound.

18. The composition of claim 1 wherein the surfactant comprises one or more polyalkylene glycol ethers, alkylarylsulfonates, amine oxides, poly(oxyalkylene) compounds, block copolymers comprising alkylene oxide repeat units, carboxylated alcohol ethoxylates, ethoxylated alkyl phenols, ethoxylated amines, ethoxylated amides, oxiranes, ethoxylated fatty acids, ethoxylated fatty esters, ethoxylated oils, fatty esters, fatty acid amides, glycerol esters, glycol esters, sorbitan esters, imidazoline and/or derivatives thereof, lecithin and/or derivatives thereof, lignin and/or derivatives thereof, glycerides and/or derivatives thereof, olefin sulfonates, phosphate esters and/or derivatives thereof, propoxylated and/or ethoxylated fatty acids and/or alcohols, alkyl phenols, sorbitan and/or derivatives thereof, sucrose esters and/or derivatives thereof, sulfates and/or alcohols and/or ethoxylated alcohols of fatty esters, sulfonates of dodecyl and/or tridecyl benzenes, condensed naphthalenes, sulfosuccinates and/or derivatives thereof, tridecyl and/or dodecyl benzene sulfonic acids, octyl betaine, or a mixture of two or more thereof.

19. The composition of claim 1 wherein the concentration of the surfactant in the supplemental medium (B) is in the range from about 5 to about 15% by weight.

20. The composition of claim 1 wherein part the supplemental medium (B) further comprises one or more scale inhibitors, preservatives, deflocuents, suspension agents, metal passivators, thickening agents, antifoam agents, foam enhancing agents, oil removal agents, sequestration agents, rheology modification agents, penetration agents, solubility agents, rinse aids, or a mixture of two or more thereof.

21. The composition of claim 1 wherein the supplemental medium (B) has a pH in the range from about 6 to about 9.

22. The composition of claim 1 wherein the volumetric ratio of (A) to (B) is from about 4:1 to about 1:4.

23. The composition of claim 1 wherein the disinfectant medium (A) is diluted with water, the volumetric ratio of water to the disinfectant medium (A) being up to about 1000:1.

24. The composition of claim 1 wherein the supplemental medium (B) is diluted with water, the volumetric ratio of water to the supplemental medium (B) being up to about 1000:1.

25. A process for cleaning and disinfecting a substrate using the two-part liquid composition of claim 1, comprising:
   (1) contacting the substrate with the supplemental medium (B) to clean the substrate, and
   (2) contacting the substrate with the disinfectant medium (A) to disinfect the substrate.

26. A process for cleaning and disinfecting a substrate using the two-part liquid composition of claim 1, comprising:

(1) contacting the substrate with the supplemental medium (B) and the disinfectant medium (A) to clean the substrate, and
(2) contacting the substrate with the disinfectant medium (A) to disinfect the substrate.

27. A process for cleaning and disinfecting a substrate using the two-part liquid composition of claim 1, comprising:
(1) contacting the substrate with the supplemental medium (B) to clean the substrate, and
(2) contacting the substrate with the disinfectant medium (A) and the supplemental medium (B) to disinfect the substrate.

28. A process for cleaning and disinfecting a substrate using the two-part liquid composition of claim 1, comprising:
(1) contacting the substrate with the supplemental medium (B) and the disinfectant (A) to clean the substrate, and
(2) contacting the substrate with the disinfectant medium (A) and the supplemental medium (B) to disinfect the substrate.

29. The process of claim 25 with the step of rinsing the substrate subsequent to step (1) but prior to step (2).

30. The process of any of claims claim 25 wherein the substrate is made of a material comprising brass, copper, aluminum, stainless steel, carbon steel, plastic, glass, or a combination of two or more thereof.

31. The process of claim 25 wherein the substrate comprises a medical, dental, pharmaceutical, veterinary or mortuary instrument or device.

32. The process of claim 25 wherein the substrate comprises an endoscope.

33. The process of claim 32 wherein the endoscope comprises a rigid endoscope.

34. The process of claim 32 wherein the endoscope comprises a flexible endoscope.

35. The process of claim 25 wherein step (1) is conducted at a temperature in the range from about 15° C. to about 60° C.

36. The process of claim 25 wherein the time required for step (1) is in the range from about 0.5 to about 240 minutes.

37. The process of claim 25 wherein step (2) is conducted at a temperature in the range from about 15° C. to about 60° C.

38. The process of claim 25 wherein the time required for step (2) is in the range from about 0.5 to about 240 minutes.

39. The composition of claim 1 wherein the enzymatic cleaner comprises a subtilisin.

* * * * *